United States Patent [19]

Wong

[11] Patent Number: 4,677,299
[45] Date of Patent: Jun. 30, 1987

[54] MULTIPLE LAYER POSITRON EMISSION TOMOGRAPHY CAMERA

[75] Inventor: Wai-Hoi Wong, Houston, Tex.

[73] Assignee: Clayton Foundation for Research, Houston, Tex.

[21] Appl. No.: 789,049

[22] Filed: Oct. 18, 1985

Related U.S. Application Data

[63] Continuation-in-part of Ser. No. 734,012, May 13, 1985.

[51] Int. Cl.⁴ .......................... G01T 1/20; G01T 1/164
[52] U.S. Cl. .................................. 250/363 S; 250/367
[58] Field of Search ............... 250/363 SA, 336, 367, 250/363 SB, 363 S, 366; 378/4, 5

[56] References Cited

U.S. PATENT DOCUMENTS

| | | | |
|---|---|---|---|
| 3,970,853 | 7/1976 | Kuhl et al. | 250/363 SB |
| 4,029,963 | 6/1977 | Alvarez et al. | 378/5 |
| 4,247,774 | 1/1981 | Brooks | 250/367 |
| 4,445,226 | 4/1984 | Brody | 378/5 |
| 4,511,799 | 4/1985 | Bjorkholm | 250/367 |
| 4,563,582 | 1/1986 | Mullani | 250/363 SA |

*Primary Examiner*—Carolyn E. Fields
*Assistant Examiner*—D. Porta
*Attorney, Agent, or Firm*—Fulbright & Jaworski

[57] ABSTRACT

A positron emission tomography camera having a patient area with a plurality of fixed detector rings positioned side-by-side around the patient area to detect radiation. Each ring includes multiple layers of scintillation detectors in which the detectors in one of the layers is offset relative to the detectors in the other layers. The thickness of each layer increases exponentially from the inside of the ring to the outside of the ring. Identification of the scintillation detector may be performed by using layers with different timing constants, using silicon avalanche photodiodes or using a light guide transferring the light received from the staggered detectors to a non-staggered rectangular matrix.

7 Claims, 10 Drawing Figures

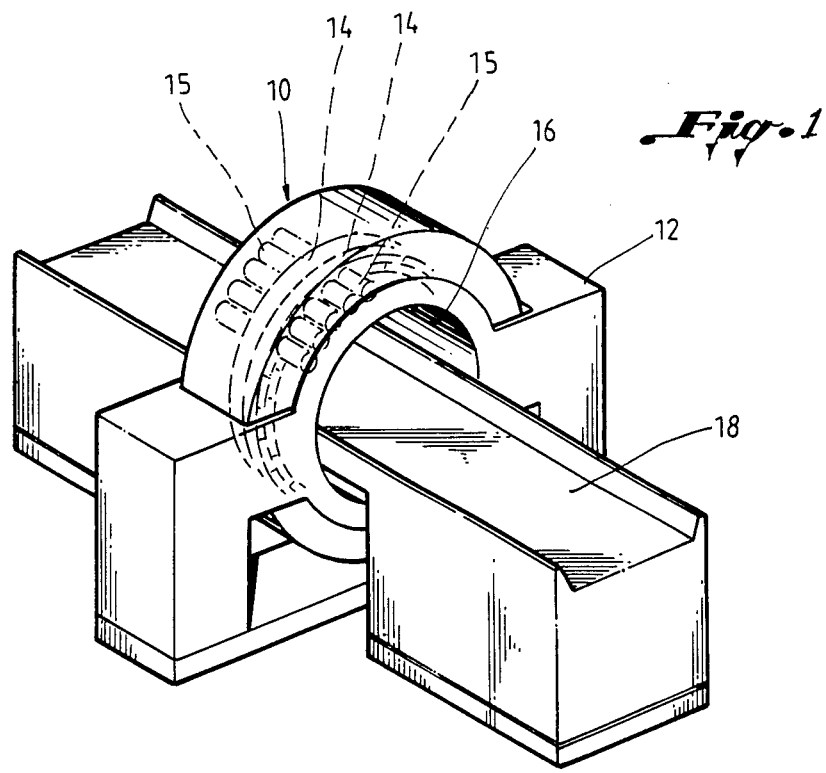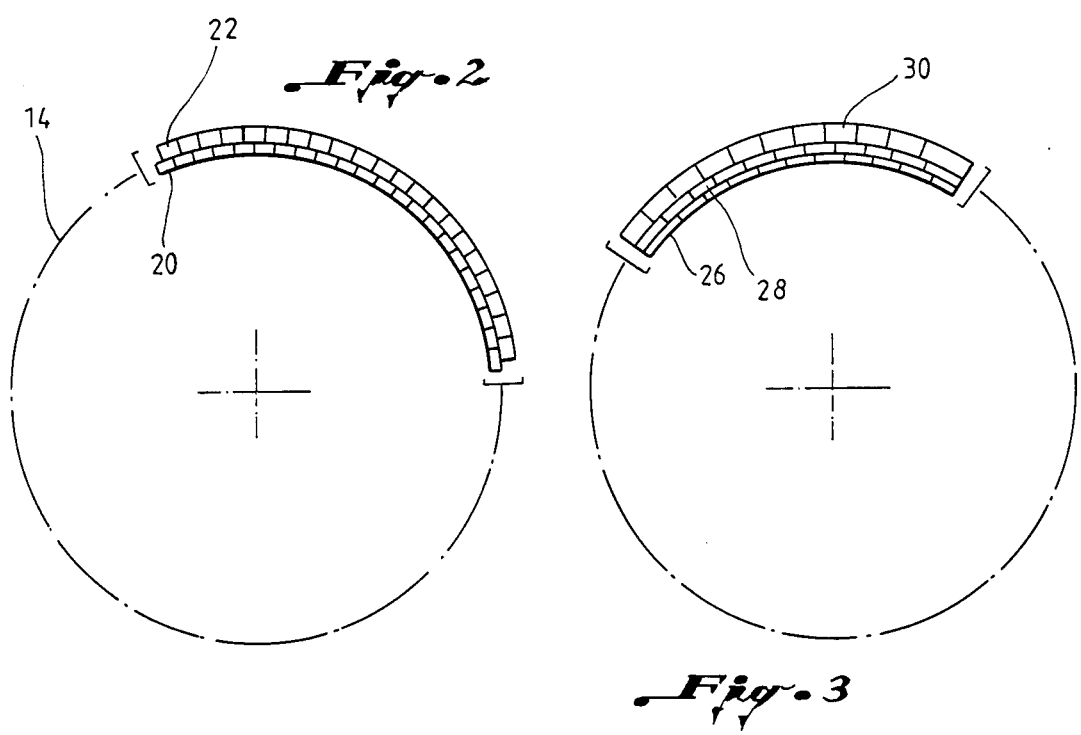

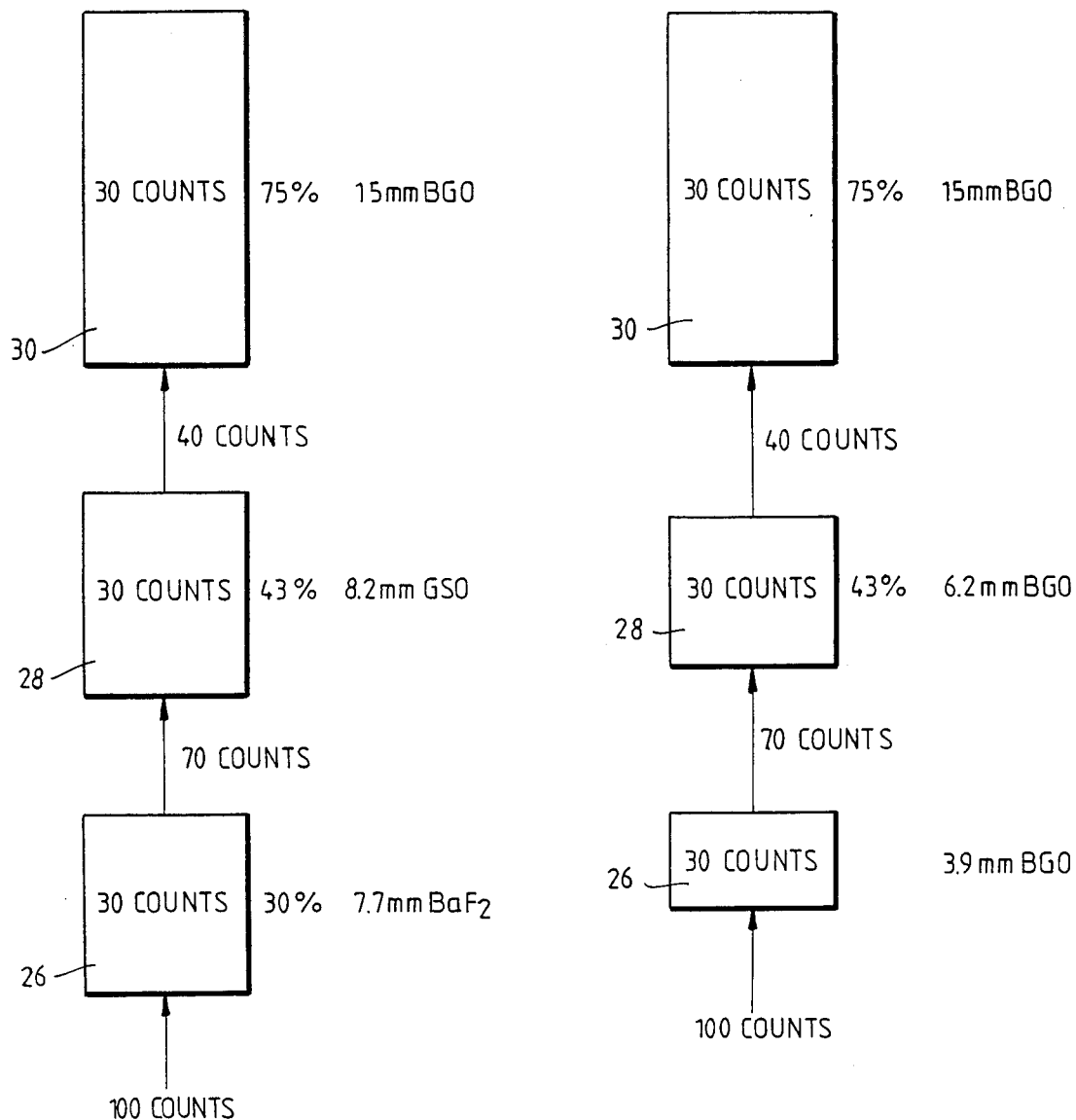

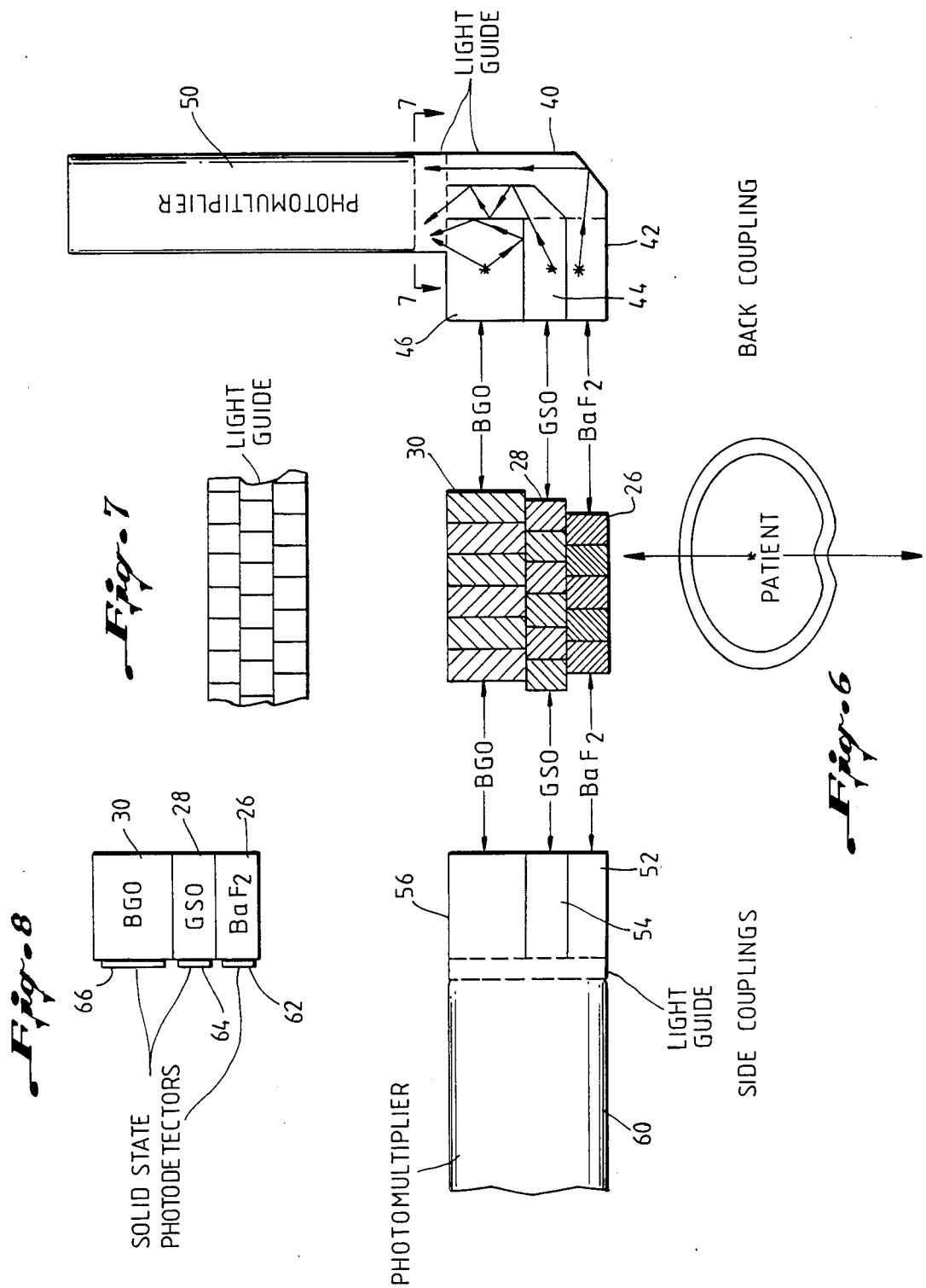

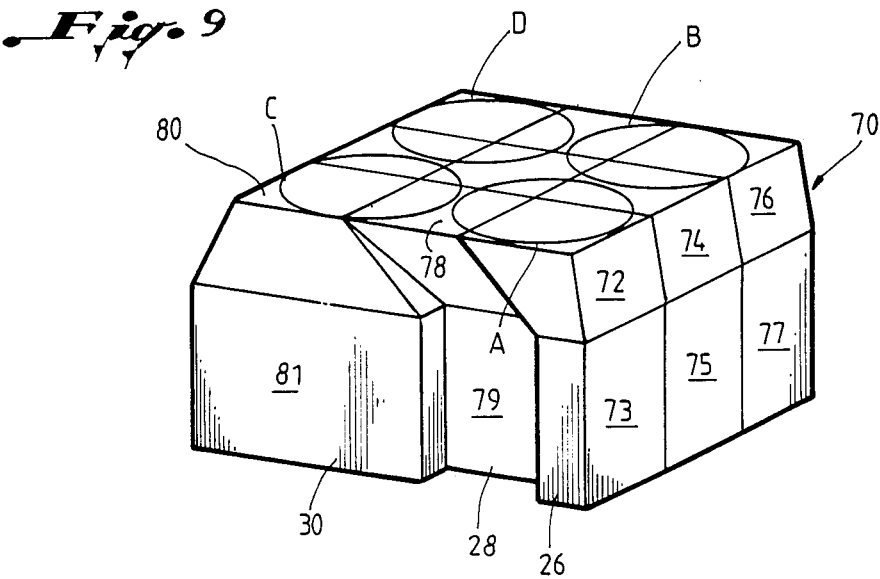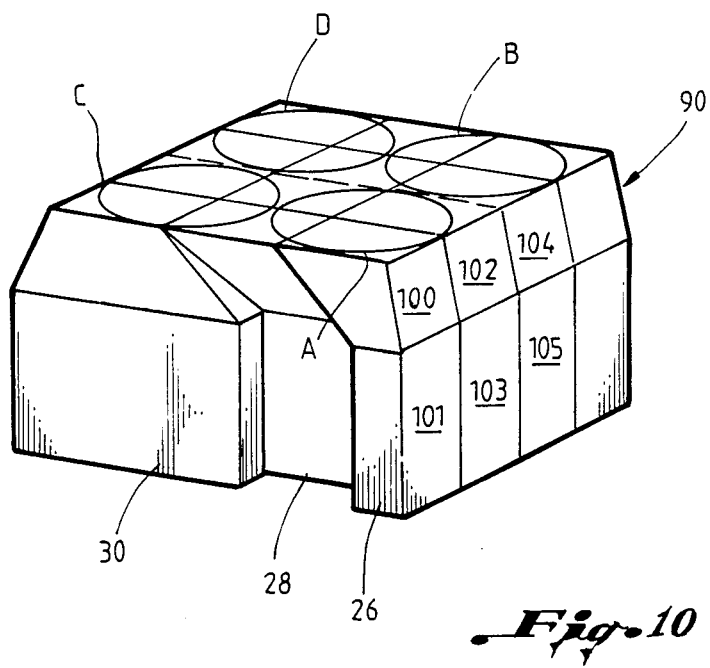

MULTIPLE LAYER POSITRON EMISSION TOMOGRAPHY CAMERA

CROSS-REFERENCE TO RELATED APPLICATIONS

This application is a continuation-in-part of Application Ser. No. 06/734,012 filed May 13, 1985, entitled Multiple Layer Positron Emission Tomography Camera.

BACKGROUND OF THE INVENTION

My above-named patent application describes a positron emission tomography (PET) camera having multiple layers of detectors or scintillators with each layer staggered or offset from its adjacent layer. That improvement structure reduces the angulation degradation thereby allowing the diameter of the detector rings to be reduced which in turn increases the camera sensitivity and reduces the detector cost. Furthermore, the multiple layers of staggered or offset detectors greatly increases the number of samples detected and allows the elimination of the conventional wobble motion from the camera.

The present invention is further directed to additional improvements in a positron emission camera (PET) having detector rings with multiple staggered or offset layers of scintillation detectors.

SUMMARY

The present invention is directed to the provision of a PET camera having a patient area and a plurality of detector rings positioned side-by-side around the patient area to detect radiation from a patient positioned in the patient area. Each ring contains a plurality of scintillation detectors directed towards the patient area for defining a plane slice through the patient area by the detectors in each ring. Each ring includes multiple layers of scintillation detectors with the detectors in one of the layers being offset relative to the detectors in the other layers in the same ring.

A still further object of the present invention is that the thickness of the layers increase from the inner layer to the outer layers and preferably exponentially from the inside to the outside of the ring to allow each layer to detect the same number of scintillation.

A still further object of the present invention is the provision of means for converting detected radiation into electrical pulses in which the means includes a light guide directed towards the side edges in which the light guide transfers the light received from the offset detectors to a non-offset rectangular matrix.

Yet still a further object of the present invention is wherein each layer of the scintillation detectors has a different timing constant for identifying the layer in which radiation is detected.

Yet still a further object of the present invention is wherein all of the layers of scintillation detectors are bismuth germante (BGO) scintillation crystals for yielding better resolution because of the smaller detector depth.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 1 is a perspective elevational view of the positron emission tomography camera of the present invention, FIG. 2 is a schematic cross-sectional view of one embodiment of the positron emission tomography camera of the present invention, FIG. 3 is a schematic elevational view, in cross section, of another embodiment of the placement of the detectors of the present invention, FIG. 4 is an expanded schematic view of one embodiment three layers of detectors of the present invention, FIG. 5 is an exploded view of another embodiment of three layers of detectors of the present invention, FIG. 6 is a schematic elevational view, in cross section, illustrating various methods of identifying which detector has detected radiation, FIG. 7 is a cross-sectional view taken along the line 7—7 of FIG. 6, FIG. 8 is an elevational view of another type of means for identifying which detector has detected radiation, FIG. 9 is a perspective view illustrating another method of determining which crystal detector has detected radiation, and FIG. 10 is yet another perspective view illustrating how four photomultiplier tubes can be used to detect which one of twelve detectors has detected radiation.

DESCRIPTION OF THE PREFERRED EMBODIMENT

Referring now to the draings, and particularly to FIG. 1, the reference numeral 10 generally indicates a positron emission tomography (PET) camera having a support or gantry 12, a plurality of detector rings, here shown as two rings 14 and 14a, for convenience, and connected photomultiplier tubes 15 and 15a, respectively, positioned side-by-side around and surrounding a patient area 16 to detect radiation therefrom. The patient area 16 may include a patient bed 18 for supporting a patient. In a PET camera, a positron isotope, such as 82 rb, is injected into the patient, each positron isotope atom then emits two gammas simultaneously and back-to-back. The detectors, which may be of various types, then capture these gammas to produce the image of the tracer distribution.

As in my copending parent application above identified, the present invention is directed to a PET camera having a plurality of rings, such as 14 and 14a, positioned side-by-side around the patient area 16 to detect radiation from a patient. Each ring 14 and 14a includes multiple layers of scintillation detectors with each layer offset or staggered from the adjacent layer. Thus referring to FIG. 2, one ring 14 is illustrated having multiple layers of scintillation detectors such as layers 20 and 22. With the two layer system shown in FIG. 2, one layer is offset or staggered relative to the other layer by half the width of one of the detectors. Referring to FIG. 3, instead of having two layers, a three layer system having layers 26, 28, and 30 are shown in which the layers are offset to the adjacent layer in the same ring by one-third of a detector width. Thus, where the number of layers of detectors are n, the offset between each adjacent layer is 1/n of the detector width. However, the total combined depth of detection material in the multiple layer systems of FIG. 2 and FIG. 3 is equal to the depth of the detector in a conventional mono-layer design to conserve the total gamma detection efficiency. The scintillation events in each detector in each layer must be uniquely identified as will be more fully discussed hereinafter. However, with the reduced depth in each layer the angulation effect which degrades the radial resolution is reduced. Given a fixed detector ring diameter, the designs of FIGS. 2 and 3 will produce the highest possible spatial resolution. Alternatively, with the reduced angulation effect, the detector ring diameter can be reduced from that of the conventional arrangement. The reduction in diameter ring size will increase the sensitivity of the camera since the camera sensitivity is linearly inversely proportional to the detector ring size. This is especially important for cameras designed for small objects, such as the brain, animals, limbs and infants.

With the detector layers staggered, the detector should be designed so that each of the layers in each ring will detect the same number of scintillation events thereby providing denser and more uniform radial sampling so that scanning movement of the detector can be eliminated. In order to achieve even sampling, each of the layers such as layers 26, 28 and 30 should stop the same number of 511 KEV events. The detector material in each layer need not be the same as long as the above condition is satisfied, although only the materials with the highest stopping power should be used. Since the attenuation of the scintillation events is exponential in nature, the inner layer 26 should be designed to have the smallest depth whereas the outer layers 28 and 30 will have increasing larger depths. Referring now to FIG. 4, a three ring layer detector system of FIG. 3 is shown for a specific embodiment having a total efficiency of about 90%. In this particular three layer design combination materials for the different layers are provided. Thus layer 26 is BAF2, while layer 28 is GSO and layer 30 is BGO detectors. It is to be noted that the depth of layer 26 is 7.7 mm, the depth of layer 28 is 8.2 mm and the depth of layer 30 is 15 mm. The particular configuration of the three layered system shown in FIG. 4 provides that each layer 26, 28 and 30 should each stop approximately 30 counts out of a 100 count event for a 90% efficiency. It is to be noted that the thickness in each of the layers 26, 28 and 30 is greater than the thickness of the adjacent inner layer. In fact, in order to insure that each of the layers 26, 28 and 30 will detect the same number of events, the layers are sized as described to provide an exponential stopping power in the first layer 26 of 30%, in the middle layer 28 of 43%, and in the outer layer 30, of 75%.

Referring now to FIG. 5, a three layer design with only BGO detectors is shown in which the thickness of the layers is increasing exponentially to provide that each layer will detect the same number of events. The three layer design with only BGO detectors should yield even better resolution because of the smaller detector depth in the two lower layers 26 and 28 as compared with the embodiment of FIG. 4.

Each of the detectors in each of the layers must be correctly identified which requires something different than the usual one photomultiplier tube to one detector as used in a conventional PET. Referring now to FIG. 6, a three layer system is shown utilizing the materials of FIG. 4 in which the staggered layers 26, 28 and 30 are of the materials BAF2, GSO and BGO, respectively. The advantage of this "phoswich" design is that the individual layers 26, 28 and 30 can be easily identified because the scintillation timing constants for the three different layers is different. Therefore, identification of the individual detectors in the layers can be performed by a photomultiplier tube (PMT) since the PMT pulse shape discrimination technique which is in common use in neutron-gamma discrimination can be used to differentiate which one of the layers 26, 28 and 30 the scintillation event occurs. After identifying the scintillation layer, one can use the conventional "analog decoding" scheme as used in the conventional MGH continuous detector ring design to identify the position of the scintillating crystal within the detected layer. FIG. 6 shows on one side of the layers 26, 28 and 30 a light guide 40 having individual light guide channels 42, 44 and 46 for the layers 26, 28 and 30, respectively, which leads to a photomultiplier tube 50 in the form of a back coupling. FIG. 6 also shows an alternate side coupling method utilizing a light guide with channels 52, 54, and 56 for use with a photomultiplier tube 60. While shown schematically in FIG. 6 the means for converting the detected radiation of the individual detectors are positioned adjacent each of the rings 14 and 14a but offset from the plane of each ring 14 and 14a and are directed perpendicularly to the plane of the ring. While the use of PMT provides an excellent and low cost device for converting the detected radiation into electrical pulses, they are quite bulky and therefore their use limits the present camera to having two rings 14 and 14a as the rings must be closely adjacent to each other to provide closely adjacent plane slices through the patient.

Referring now to FIG. 8, again a three layer crystal detector system is used having layers 26, 28 and 30 in which a plurality of silicon avalanche photodiodes 62, 64, and 66 are provided adjacent each of the individual detectors. This type of photodiode has the advantage of being small enough so that more than two rings 14 and 14a of detectors may be utilized to provide a multiplicity of adjacent plane slices through a patient. A disadvantage of the silicon avalanche photomultipliers is their high cost.

Hence with the use of both the "phoswich" and analog decoding schemes, the number of PMT used in a system can be minimized. This together with the fixed detector system and smaller ring diameter allowed by this design will allow a rather inexpensive PET camera to be constructed. The other approach of detector location is the use of the silicon avalanche photodiodes, FIG. 8, with one diode per scintillator. The compactness of the photodiodes permits the one diode per scintillator approach and also allows more than two detector rings to be constructed. Using such an approach, all of the layers can be made of BGO as shown in FIG. 5 to get the best possible resolution because of less detector depth in the inner layers.

A third way to couple the PMT to the multilayer staggered layers 26, 28 and 30 of scintillators is shown in FIG. 9 in which all of the layers 26, 28 and 30 are made up of GBO crystal scintillators and are offset as shown in FIG. 3 and have the different depths as shown in FIG. 5. A light guide generally indicated by the reference numeral 70 is provided on the side of the layers 26, 28 and 30 to transfer the light from the staggered and offset and different depth crystals to a non-staggered rectangular matrix of 3×3 so that four PMT's A, B, C and D may use to decode the nine possible positions of scintillation. Thus, when light guide 72 receives a flash because of a scintillation in crystal 73 only PMT A receives a signal. When light guide 74 receives a flash from a scintillation in crystal 75, PMT A and B receives signals. When light guide 76 receives a signal from crystal 77, only PMT B receives a signal. When light guide 78 receives a signal from crystal 79 PMT A and C receives signals. And when light guide 80 receives a signal from crystal 81 in layer 30 only PMT C receives a signal. The remainder of the light guides are similar so that nine crystals may be identified with four PMT's for decoding the position of scintillation in the nine crystal detectors in the layers 26, 28 and 30.

The arrangement of FIG. 9 provides a crystal identification which is almost as positive as having one PMT/scintillator. In addition the scintillator/PMT ratio of three compensates for the threefold increase in the number of scintillators in a three layer design but without a threefold increase in the number of PMT's.

Referring now to FIG. 10, a light guide generally indicated by the reference numeral 90 is provided to transfer light from layers 26, 28 and 30 of crystal detectors, all of which may be of the same type, in which the light guide 70 transfers the light from a staggered and different depth size crystal into a non-staggered rectangular matrix in order that four PMT's may be used to decode the position of scintillation in twelve crystals. That is, again the light guide 90 is shaped to transfer the light from a plurality of irregularly positioned and shaped crystals to a regular matrix. Thus when light guide 100 receives light from crystal 101 only PMT A receives a signal. When light guide 102 receives light from crystal 102 PMT A receives a signal but also PMT B receives a signal since light guide 104 has an interconnection with light guide 102. However, since the signal in PMT A will be larger than that of PMT B this will be an indication of a signal from crystal 103. On the other hand, when light guide 104 receives a signal from crystal 105, again both PMT A and PMT B receives signals, but in this case the larger signal is received by PMT B which defines light guide 104. The remainder of the light guide 90 is similarly designed to allow four PMT's to define the actual scintillator location.

The present invention provides a staggered-exponential depth multilayer detection system for PET cameras. This detection system can improve the image resolution to the theoretical limit of positron range (2-3 mm) throughout the entire field of view with a detector ring no bigger than that of the conventional design. Alternatively, the system can be used to build a higher sensitivity PET (2.5 times that of conventional) with the use of half size detector ring in which the ring can be motionless. Such a fixed half size detector ring is less expensive, simpler, and especially suitable for PET's for scanning small object. With the existing photomultiplier technology of one PMT/scintillator only a maximum of two rings (three image planes) can be provided. However, with the present system, and without wobbling, it is possible to translate the detector along the z-axis fast enough to capture three additional slices or double the axial FOV in the object. Hence a very inexpensive PET with two miniaturized rings of detectors can provide true three-dimensional imaging with an axial FOV equivalent to six slices and with little sacrifice and sensitivity and resolution.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will be readily apparent to those skilled in the art and which are encompassed within the spirit of the invention and the scope of the appended claims.

What is claimed is:

1. A positron emission tomography camera comprising, a patient area, a plurality of detector rings positioned side-by-side around the patient area to detect radiation from opposite sides of a patient in the patient area, each ring containing a plurality of scintallation detectors directed towards the patient area for defining a plane slice through the patient area by the detectors in each ring, said detectors on opposite sides of the patient detecting two oppositely directed gamma rays, each ring including multiple layers of scintillation detectors, the detectors in one of the layers being offset relative to the detectors in the other layers in the same ring, and the thickness of each layer being greater than the thickness of the next inner layer and the thickness of each layer being sized so that each layer detects substantially the same number of gamma rays.

2. The apparatus of claim 1 wherein the detectors are of the same material and the thickness of the multiple layers increase exponentially from the inner layers of the outer layers.

3. The apparatus of claim 1 wherein each layer of scintillation detectors has a different timing constant for identifying the layer in which radiation is detected.

4. The apparatus of claim 1 including, means for converting detected radiation into electrical pulses, said means including a light guide directed towards the side edges of said rings, said light guide transferring the light received from the offset detectors to a non-offset rectangular matrix.

5. The apparatus of claim 1 wherein all of the layers of detectors are GBO crystal scintillation detectors.

6. The apparatus of claim 1 wherein the number of layers of detectors are n and the offset between each adjacent layer is 1/n of the detector width.

7. A positron emission tomography camera comprising, a patient area, a plurality of fixed circular detector rings positioned side-by-side around the patient area to detect radiation from opposite sides of a patient in the patient area, each ring containing a plurality of scintillation detectors, said detectors on opposite sides of the patient detecting two oppositely directed gamma rays, the detectors in one of the layers being offset relative to the detectors in the other layers in a ring for increasing the sampling of detected radiation, said number of layers of detectors being n and the offset between each adjacent layer is 1/n of the detector width, and the thickness of each layer being increased over the adjacent inner layer and the thickness of each layer being sized so that each layer detects substantially the same number of gamma rays.

* * * * *

UNITED STATES PATENT OFFICE
CERTIFICATE OF CORRECTION

PATENT NO. : 4,677,299
DATED : June 30, 1987
INVENTOR(S) : Wai-Hoi Wong

It is certified that error appears in the above-identified patent and that said Letters Patent are hereby corrected as shown below:

Column 2, line 33, delete "draings" and insert -- drawings --

Column 4, line 57, delete "GBO" and insert -- BGO --

Column 5, line 22, delete "PMT"s" and insert -- PMT's --

Column 6, line 29, delete "of" and insert -- to --

Column 6, line 41, delete "GBO" and insert -- BGO --

Signed and Sealed this

Fifth Day of January, 1988

*Attest:*

DONALD J. QUIGG

*Attesting Officer*  *Commissioner of Patents and Trademarks*